US006211405B1

(12) United States Patent
Cheung et al.

(10) Patent No.: US 6,211,405 B1
(45) Date of Patent: Apr. 3, 2001

(54) ADDITION OF IRIDIUM TO THE RHODIUM/ INORGANIC IODIDE CATALYST SYSTEM

(75) Inventors: Hung-Cheun Cheung; Elaine C. Sibrel, both of Corpus Christi, TX (US); Robin S. Tanke, Stevens Point, WI (US); G. Paull Torrence, Corpus Christi, TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 09/178,325

(22) Filed: Oct. 23, 1998

(51) Int. Cl.$^7$ .................................................. C07C 51/12
(52) U.S. Cl. ........................ 562/519; 560/232; 562/890
(58) Field of Search .................................. 562/519, 890; 560/232

(56) References Cited

U.S. PATENT DOCUMENTS

| | | |
|---|---|---|
| 3,769,329 | 10/1973 | Paulik et al. . |
| 4,994,608 | 2/1991 | Torrence et al. . |
| 5,001,259 | 3/1991 | Smith et al. . |
| 5,026,908 | 6/1991 | Smith et al. . |
| 5,144,068 * | 9/1992 | Smith et al. . |
| 5,155,265 | 10/1992 | Scates et al. . |
| 5,155,266 | 10/1992 | Scates et al. . |
| 5,202,481 | 4/1993 | Scates et al. . |
| 5,206,434 | 4/1993 | Scates et al. . |
| 5,371,286 | 12/1994 | Blay et al. . |
| 5,625,094 * | 4/1997 | Nobel et al. . |
| 5,723,660 * | 3/1998 | Morimoto et al. . |
| 5,783,731 | 7/1998 | Fisher et al. . |

FOREIGN PATENT DOCUMENTS

| | | | |
|---|---|---|---|
| 31 96-7-293 | 3/1994 | (CA) | ............................. C07C/53/00 |
| 0 849 251 | 12/1997 | (EP) | ............................. C07C/51/12 |
| 618183 | 10/1994 | (FR) . | |
| 643034 | 3/1995 | (GB) . | |
| 2 298 200 | 2/1996 | (GB) | ............................. C07C/51/12 |
| 752406 | 1/1997 | (GB) . | |
| 846674 | 6/1998 | (GB) . | |
| 849248 | 6/1998 | (GB) . | |
| 98/22420 | 11/1997 | (WO) | ............................. C07C/51/12 |

OTHER PUBLICATIONS

Applied Industrial Catalysis, vol. 1 257 (1983).
Ind. Eng. Chem., Prod.Res.Dev., vol. 16, No. 4, 281 (1977).
Advances in Catalysis, vol. 34, 81 (1986).
J. Chem. Soc., Dalton Trans., 1997, pp. 1639–1645.

* cited by examiner

Primary Examiner—James O. Wilson
Assistant Examiner—Robert W. Deemie
(74) Attorney, Agent, or Firm—M. Susan Spiering

(57) ABSTRACT

The present invention provides a process for the carbonylation of an alcohol, ether or ester to products comprising a carboxylic acid, the anhydride thereof or coproduction of the carboxylic acid and anhydride. More particularly, the present invention provides a process for the carbonylation of methanol to produce acetic acid by reacting methanol with carbon monoxide in a liquid reaction medium containing a catalyst comprising rhodium, iridium, iodide ion, and said reaction medium further comprising water, acetic acid, methyl iodide, and methyl acetate and subsequently recovering acetic acid from the resulting reaction product.

12 Claims, No Drawings

ADDITION OF IRIDIUM TO THE RHODIUM/INORGANIC IODIDE CATALYST SYSTEM

FIELD OF THE INVENTION

The present invention relates to homogeneous carbonylation catalyst systems, and more particularly to multimetal homogeneous carbonylation catalyst system stabilized and co-promoted with a soluble inorganic iodide salt, in particular, an alkali metal or alkaline earth metal salt or quaternary iodide salt of nitrogen or phosphorus.

DESCRIPTION OF RELATED ART

Producing acetic acid by means of methanol carbonylation with a rhodium salt catalyst is a well-known commercial process as disclosed in U.S. Pat. No. 3,769,329 issued by Paulik et al. and described by Eby and Singleton (*Appl. Ind. Catal.* 1,275, (1983). U.S. '329 discloses the use of organic halides such as methyl iodide to promote the reaction. It is stated in U.S. '329 that a substantial quantity of water, typically about 14–15 wt % is necessary to attain a high reaction rate. Hjortjaer and Jensen (*Ind. Eng. Chem; Proc. Res. Dev.* 16, 281–285 (1977)) have shown that increasing the reaction water from about a finite amount to about 14 wt % increases the reaction rate of methanol carbonylation. However having a large amount of water present in the process incurs an expensive operating cost to separate water from the acetic acid product desired.

It has been found that under the Paulik et al. conditions at lower than 14–15 wt % water content in a carbonylation reaction system, the carbonylation rate decreases significantly and the rhodium catalyst tends to destabilize and thus precipitate out of the reaction system.

U.S. Pat. Nos. 5,001,259; 5,026,908; and 5,144,068, Smith et al., disclose a method to solve the difficulties of high reaction water and catalyst destabilization described above. These patents disclose the use of a rhodium salt catalyst in a low water carbonylation system, i.e., water concentration from at least a finite amount to less than 14 wt %, preferably less than 7 wt %. The carbonylation reaction is further promoted and the catalyst is stabilized to prevent precipitation by using a soluble alkali or alkaline earth metal iodide salt, i.e, such as lithium iodide, or by using a soluble quaternary ammonium or phosphonium iodide salt.

A disadvantage of the process described in U.S. '259 et al. is described in U.S. Pat. No. 5,155,265; U.S. Pat. No. 5,155,266; U.S. Pat. No. 5,202,481; U.S. Pat. No. 5,206,434; U.S. Pat. Nos. 5,371,286, and 5,783,731. The process increases the concentration of iodide, unsaturates, and carbonyl impurities. These patents stress the necessity to remove these impurities from the process.

Another disadvantage of the process of U.S. '259 et al. is that as the water content is decreased, so is the rate of reaction. Therefore efforts have been directed at maintaining and increasing the rate of reaction under water conditions of less than 14–15 wt %. A method of increasing the rate of reaction, as shown in the U.S. '608, is to increase the hydrogen partial pressure in the reaction system. Increasing hydrogen partial pressure can be accomplished by having hydrogen in the carbon monoxide feedstock fed to the carbonylation reaction. Commercial carbon monoxide feedstocks frequently contain hydrogen as an impurity, and under normal circumstances, there is no need to remove these impurities.

U.S. Pat. No. 4,994,608 stresses the necessity to control the hydrogen in the carbon monoxide feed to reduce the formation of carbon dioxide. In addition to having hydrogen present in the carbon monoxide feed, hydrogen can be generated in-situ by the competing water-gas shift reaction that occurs during the reaction. Thus, because of the formation of this in-situ hydrogen, the amount of hydrogen in the carbon monoxide feed is suggested in U.S. '608 to be from about 0.3 to about 10 mol %.

The iridium-catalyzed methanol carbonylation process as described in EP 752,406 stresses the necessity to maintain a low hydrogen concentration in the carbon monoxide feed to the reactor to avoid the formation of hydrogenated by-products. Iridium is a strong hydrogenation catalyst under the conditions of the iridium-catalyzed process. Therefore, the amount of hydrogen in the carbon monoxide feed is suggested in EP '406 to be less than 0.3 mol % and the partial pressure of hydrogen in the carbonylation reactor to be less than 0.3 bar.

Methods disclosed in the art to enhance the rate of carbonylation with catalysts containing rhodium include the use of promoters. EP 643,034 describes the use of ruthenium or osmium as co-promoters. EP 618,813 broadly describes the use of rhodium as a promoter to enhance the rate of iridium catalyzed carbonylation reactions. Similarly, GB 2,298,200 broadly describes the use of ruthenium, osmium, or rhenium with rhodium also as a co-promoter to enhance the iridium-catalyzed carbonylation reaction.

However, it is not clear from these references whether iridium could be added to a rhodium-catalyzed system when inorganic iodide salts are present. Ionic iodides, such as the alkali or alkaline earth metal iodides, had been previously thought to inhibit and consequently deactivate the iridium catalyst. Dekleva and Forster in *Adv. Catalysis*, 34, 81 (1986) and references cited therein, particularly Forster, *J. Chem. Soc., Dalton Trans.*, 1979, p. 1639, have indicated that ionic iodides decrease the rate of methanol carbonylation when an iridium catalyst is employed.

The use of rhodium salt and iridium salt catalysts for methanol carbonylation is disclosed in Canadian 2,120,407 and GB 2,298,200. Can '407 and GB '200 also teach that ionic iodides poison the iridium catalyst. It is suggested therein to limit the amount of ionic iodides from 0 to about 2 wt %. Sources of ionic iodides include: 1) from alkali or alkaline earth metals as a promoter; 2) from corrosion metals common in the reaction system; and 3) from phosphonium or ternary ammonium ions as promoters.

More recent patent publications also teach that the use of alkali metal iodides and alkaline earth iodides are to be avoided in the iridium-catalyzed carbonylation. These references include WO 98/22420, EP 846 674 A1, EP 849 248 A1, EP 849 251 A1. Although, EP 849 248 A1 indicates that under certain conditions wherein the water concentration in the reactor is at or below that at which the maximum in the graph of carbonylation rate versus water concentration occurs, iodides of alkali metals and alkaline earth metals may be added. It is taught that under these conditions the presence of iodide ion in high concentration may be detrimental, when the carbonylation catalyst is solely iridium. No mention therein is made of the use of alkali metal or alkaline earth metal iodides in a mixed rhodium-iridium catalyzed carbonylation reaction by generating iodide ions in the liquid reactor composition.

EP 752,406 cautions to minimize the ionic contaminants derived from corrosion metals, particularly, nickel, iron and chromium, or phosphines and nitrogen containing compounds, or ligands which may quaternize in situ due to the belief that these ions also poison the iridium salt catalyst system. The poisoning occurs by generating iodide ion in the liquid reaction composition which has an adverse effect on the reaction rate.

The present invention addresses the technical difficulties described above. Disclosed is a method to improve the rate of carbonylation while maintaining the stability of the rhodium catalyst and limiting the formation of impurities.

SUMMARY OF THE INVENTION

The present invention relates to a process for producing a carboxylic acid by carbonylation of an alkyl alcohol and/or a reactive derivative thereof, i.e. an alkyl ester or ether, in the presence of a homogeneous catalyst of rhodium salt, an ionic iodide catalyst stabilizer/co-promoter, iridium salt, and an alkyl iodide promoter. The ionic iodide stabilizer/co-promoter may be in the form of a soluble salt of an alkali metal or alkaline earth metal salt or a quaternary ammonium or phosphonium salt that will generate an effective amount of iodide ion in the reaction solution. The stabilizer/co-promoter is preferably a soluble iodide salt from alkali metals or alkaline earth metals, in particular lithium iodide. Alternatively, the stabilizer may be a soluble quaternary ammonium or phosphonium iodide salt. The alkyl halide is preferably methyl iodide.

DETAILED DESCRIPTION OF THE DISCLOSURE

More particularly, the present invention provides a process for the carbonylation of an alcohol, ether, or ester to products comprising a carboxylic acid, the anhydride thereof or co-production of the carboxylic acid and anhydride. Even more particularly, the present invention provides a process for the carbonylation of methanol to produce acetic acid by reacting methanol with carbon monoxide in a liquid reaction medium containing a catalyst comprising rhodium salt, an ionic iodide stabilizer/co-promoter, and iridium salt; water, acetic acid, methyl iodide promoter, and methyl acetate; and subsequently recovering acetic acid from the resulting reaction product. The process is conducted so as to maintain in the reaction medium during the course of the reaction about a finite amount to less than 14 wt % of water together with (a) a salt providing an effective amount in the range of about 2 wt % to 20 wt % of an ionic iodide in the reaction solution as a catalyst stabilizer/co-promoter selected from the group consisting of alkali and alkaline earth metal salts and/or quaternary salt of nitrogen or phosphorus.

(b) about 5 wt % to 30 wt % of methyl iodide, and (c) about 0.5 wt % to 30 wt % of methyl acetate.

The ionic iodide stabilizer/co-promoter may be in the form of a soluble salt from alkali metal or alkaline earth metal salt or a quaternary ammonium or phosphonium salt which generates an effective amount as defined above of iodide ion in the reaction solution. The catalyst stabilizer/co-promoter is preferably lithium iodide, lithium acetate or mixtures thereof. The catalyst system can further comprise a transition metal salt as a co-promoter selected from the group consisting of salts of ruthenium, tungsten, osmium, nickel, cobalt, platinum, palladium, manganese, titanium, vanadium, copper, aluminum, tin, and antimony.

The present invention may include hydrogen, generally added in conjunction with the carbon monoxide feedstock to the carbonylation reactor. It has been found that the presence of hydrogen increases rate of reaction, and minimizes formation of organic impurities.

An advantage of the present invention is that a higher carbonylation rate is achieved when adding iridium salt to the catalyst system comprising rhodium salt and an alkali metal or alkaline earth metal salt, and/or soluble quaternary ammonium or phosphonium salts, providing an effective amount in the range of about 2 wt % to 20 wt % of an ionic iodide in the reaction solution over using rhodium salt alone. The stabilizer/co-promoter has been found to stabilize the rhodium/iridium catalyst without precipitation occurring during the carbonylation reaction and provides additional catalyst activity.

Another advantage of the present invention is that the production of impurities such as acetaldehyde and especially unsaturated aldehydes such as crotonaldehyde and 2-ethyl crotonaldehyde is significantly reduced when rhodium/iridium/iodide ion catalyst system is employed using conditions equivalent to those used with the rhodium/iodide salt catalyst system alone. Such an advantage improves product quality and reduces the need for additional purification to remove impurities.

DESCRIPTION OF ILLUSTRATIVE EMBODIMENTS

The present invention provides an improvement on carbonylation processes wherein an alcohol, ester, or ether is converted to a carboxylic acid and/or the anhydride thereof. The following description is directed to the carbonylation of methanol to produce acetic acid. However, the technology is applicable to the carbonylation of higher homologues of methanol to form acids which are the higher homologues of acetic acid. A previously used methanol carbonylation process comprises reacting methanol with carbon monoxide in a liquid reaction medium containing a rhodium salt catalyst and comprising water, acetic acid, methyl iodide promoter, methyl acetate, and ionic iodide stabilizer/co-promoter and subsequently recovering acetic acid from the resulting reaction product. As described hereinabove, a previously used methanol carbonylation process included the use of iridium salt catalyst, plus the other components mentioned in conjunction with the rhodium catalyzed system except for acknowledging the benefit of the iodide salt. In the present invention, the metal catalyst comprises rhodium and iridium, and the reaction medium further includes an alkali or alkaline earth metal iodide salt and/or a quaternary ammonium or phosphonium iodide salt as a catalyst stabilizer/co-promoter. The metal catalyst can also include other transition metals. The carbonylation reaction system may further include hydrogen in the carbon monoxide feed. Hydrogen from greater than about 5 ppm with iridium does not have significant effect on production of unsaturates. This allows one to use $H_2$ if desired in the CO feed or reaction medium. With respect to production of propionic acid, hydrogen has a significant effect. Therefore, low hydrogen in the reaction medium may be more desirable depending on impurity production.

The metal catalyst can be added to the liquid reaction composition for the carbonylation reaction in any suitable form which dissolves in the liquid reaction composition or is convertible to a soluble form. The amount of rhodium added to the reaction medium is generally between about 100 and 5000 ppm, and is preferably between about 300 and 1000 ppm. Examples of the rhodium catalyst are well known to those skilled in the art and were best described in the Paulik et al. U.S. '329 patent. The amount of iridium salt added to the reaction medium is generally between about 100 and 5000 ppm, and preferably between about 200 and 2000 ppm. Examples of suitable iridium-containing salts which may be added to the liquid reaction composition include iridium acetate, iridium oxalate, iridium acetoacetate, iridium metal, $IrCl_3$, $IrI_3$, $IrBr_3$, $IrCl_3.3H_2O$, $IrBr_3.3H_2O$, $Ir_2O_3$, $IrO_2$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO)_2]^-H^+$, and $Ir_4(CO)_{12}$., preferably complexes of iridium such as acetates, oxalates and acetoacetates which are soluble in one or more of the carbonylation reaction components such as water, alcohol and/or carboxylic acid.

Other transition metal salts may be added to the reaction medium as well. Such transition metal salts may include salts of ruthenium, tungsten, osmium, nickel, cobalt, platinum, palladium, manganese, titanium, vanadium, copper, aluminum, tin, and/or antimony salts. Generally, the amount of these transition metal salts is between about 100 and 4000 ppm.

Any alkali metal or alkaline earth metal salt, such as salts of lithium, potassium, magnesium, and calcium, can be used as a catalyst stabilizer/co-promoter provided that the salt is sufficiently soluble in the reaction medium to provide or generate an effective amount of a soluble ionic iodide for the desired level of catalyst stabilization/promotion. In particular, lithium salts, such as lithium iodide and lithium acetate, are useful, with lithium iodide being preferred. The concentration of the iodide ion in the reaction medium is generally between about 2 and 20 wt %, preferably between about 10 and 20 wt %.

The concentration of water in the reaction medium is typically between about a finite amount (>50 ppm) and 14 wt %. The concentration of water is preferably between about 0.1 and 8 wt %, and most preferably between about 0.5 and 4 wt %. The concentration of methyl acetate in the reaction medium is generally between about 0.5 and 30 wt %, preferably between about 1 and 20 wt %. The concentration of methyl iodide in the reaction medium is typically between about 5 and 30 wt %, preferably between about 5 and 15 wt %. Acetic acid typically makes up the balance of the reaction medium.

The carbon monoxide partial pressure in the carbonylation reactor is typically about 2 to 30 atmospheres absolute, preferably about 5 to 20 atmospheres absolute. Because of the partial pressure of byproducts and the vapor pressure of the contained liquids, the total reactor pressure is from about 15 to 45 atmospheres absolute, with the reaction temperature being approximately 150 to 250° C. Preferably, the reactor temperature is about 175 to 220° C.

The carbon monoxide feed to the carbonylation reactor can contain hydrogen. Commercial carbon monoxide feedstocks frequently contain low levels of hydrogen as an impurity, and there is no need here to attempt to remove such impurities. The addition of iridium to the rhodium/iodide ion system in the present invention decreases the formation of the aldehyde by-products. Iridium acts as an efficient hydrogenation catalyst in the present reaction wherein the hydrogen is provided from the water gas shift reaction or from hydrogen in the carbon monoxide feed or both.

One advantage of the present invention is that a higher carbonylation rate is achieved when adding iridium salt to the catalyst system comprising rhodium salt and an iodide ion as from an alkali metal or alkaline earth metal iodide salt or a quaternary ammonium or phosphonium iodide salt over using rhodium salt in the absence of such stabilizer/co-promoters. A further advantage of the present invention is that the addition of iridium salt or iridium salt and ruthenium to a catalyst system comprising rhodium salt and an alkali or alkaline earth metal iodide salt or a quaternary ammonium or phosphonium iodide salt has been found to reduce the production of acetaldehyde and all impurities derived from acetaldehyde, especially unsaturated aldehydes such as crotonaldehyde and ethyl-crotonaldehyde.

A typical reaction system which can be employed for the process of the present invention comprises (a) a liquid-phase carbonylation reactor, (b) a flasher, and (c) a methyl iodide-acetic acid splitter column. The carbonylation reactor is typically a stirred autoclave within which the reacting liquid contents are maintained automatically at a constant level. Into this reactor there are continuously introduced fresh methanol, sufficient water to maintain at least a finite concentration of water in the reaction medium, recycled catalyst solution from the flasher base, and recycled methyl iodide and methyl acetate from the overhead of the methyl iodide-acetic acid splitter column. A distillation system can be employed to process the condensed overhead stream from the flasher. The residue from the flasher is recirculated to the reactor. Carbon monoxide is continuously introduced into and thoroughly dispersed within the carbonylation reactor. A gaseous purge stream is vented from the head of the reactor to prevent buildup of gaseous by-products and to maintain a set carbon monoxide partial pressure at a given total reactor pressure. The temperature and pressure of the reactor are kept constant by methods known in the art.

Crude liquid product is drawn off from the carbonylation reactor at a rate sufficient to maintain a constant level therein and is introduced to the flasher at a point intermediate between the top and bottom thereof. In the flasher the catalyst solution is withdrawn as a base stream predominantly acetic acid containing the rhodium catalyst and the iodide salt along with lesser quantities of methyl acetate, methyl iodide, and water, while the condensed overhead of the flasher comprises largely the crude product, acetic acid, along with methyl iodide, methyl acetate, and water. A portion of the carbon monoxide along with gaseous by-products such as methane, hydrogen, and carbon dioxide exits the top of the flasher.

The product acetic acid is drawn from the base of the methyl iodide-acetic acid splitter column (it can also be withdrawn as a side stream near the base) for final purification as desired by methods which are obvious to those skilled in the art and which are outside the scope of the present invention. The overhead from the methyl iodide-acetic acid splitter, comprising mainly methyl iodide and methyl acetate, is recycled to the carbonylation reactor.

Experiments confirmed the findings in the art that iridium plus iodide ion resulted in minimal to no rate of reaction. In particular, it was found that about 10 wt % iodide ion plus iridium resulted in no reactivity. However, the addition of iridium salt to an rhodium/iodide ion catalyst system did not produce the expected inactivity of iridium caused by the iodide ion, but provided a significant enhancement of the catalyst activity. This finding of adding iridium to a rhodium/iodide ion system as a rate promoter in a methanol carbonylation system was surprising and unexpected. Also surprising and unexpected was the significant reduction in the formation of aldehyde impurities, i.e., acetaldehyde, crotonaldehyde, and 2-ethyl crotonaldehyde.

Additionally, use of hydrogen in combination with rhodium/iridium/iodide ion catalyst system increased the rate of reaction while the impurities remained relatively unchanged when compared to rhodium/iodide ion catalyst system.

The use of additional transition metals such as ruthenium, tungsten, and like (as described above) was found advantageous. A catalyst system comprising rhodium/iridium/ruthenium/iodide ion catalyst system was found to produce increased rate of reaction with impurities of the reaction remained relatively unchanged.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

To a 300 cc Hastalloy B autoclave was added water, glacial acetic acid (Fisher ACS grade), anhydrous lithium iodide (Alfa), rhodium triiodide (Engelhard, 21.28% Rhodium), methyl acetate (Aldrich) and methyl iodide (Fisher). The weight per cent of reactants in the autoclave was as follows: water, 3%; lithium iodide, 0 or 10% as indicated in Table I; methyl acetate, 27%; methyl iodide, 20%; and acetic acid as balance. The amount of rhodium used is indicated in Table 1. Iridium salt was also added as iridium oxide ($IrO_2$) in an amount indicated in Table I. After the autoclave was charged with the appropriate components, it was pressured to 50 psig with carbon monoxide and slowly bled off; this step was repeated two additional times. The autoclave was then pressure tested for ten minutes at 400 psig. The pressure was slowly bled to about 270 psig and an electric heater applied heat. As the internal reactor temperature reached the target temperature of 195° C., the pressure was adjusted to about 400 psig by adding carbon monoxide from a high-pressure reservoir as needed. When the reactor solution again reached 195° C., the stirrer was turned on at about 800 rpm and time zero was established for the carbonylation reaction. The measure of change in pressure of the carbon monoxide reservoir with time was used as a direct indication of the rate of carbonylation. A temperature of 195° C. and pressure of 400 psig were maintained for 30 minutes. The results of the reaction rate, reported as the space-time yield (STY) of carbon monoxide measured as moles of carbon monoxide per liter of reaction solution per hour (mol./L-hr.), are given in Table I.

Batch results in Table I illustrate the advantage of an rhodium/iridium/iodide ion catalyst system (B–C) over a rhodium/iridium catalyst system without iodide ion (A). The same table shows that 1000 ppm iridium added to rhodium/iodide ion catalyst system significantly raises the carbonylation rate from 18 to 22 (mol/L-hr). The promotional effect of iridium in the rhodium/iodide ion catalyst system is compared in lines B vs. F. The ineffectiveness of the iridium/iodide ion catalyst system at as low as 1 and 2 wt % iodide ion compared to the iridium catalyst system without iodide ion salt is shown in lines D and E vs. G and H of Table 1.

TABLE I

Batch autoclave results

| Catalyst | LiI (wt %) | Rh (ppm) | Ir (ppm) | STY (mol/L-hr) |
|---|---|---|---|---|
| A Rh/I⁻ | 10 | 600 | 0 | 18 |
| B Rh/I⁻/Ir | 10 | 600 | 1000 | 22 |
| C Rh/Ir | 0 | 600 | 1000 | 20 |

TABLE I-continued

Batch autoclave results

| Catalyst | LiI (wt %) | Rh (ppm) | Ir (ppm) | STY (mol/L-hr) |
|---|---|---|---|---|
| D Ir/I⁻ | 1 | 0 | 1000 | 3 |
| E Ir/I⁻ | 2 | 0 | 1000 | 0 |
| F Ir/I⁻ | 10 | 0 | 1000 | 0 |
| G Ir | 0 | 0 | 1000 | 10 |
| H Ir | 0 | 0 | 2333 | 24 |

EXAMPLE 2

Continuous methanol carbonylations were performed in a reaction system as described previously, wherein a liquid-phase carbonylation reactor was used, followed by a flasher, and then a methyl iodide-acetic acid splitter column. The reactant composition for each system is given in Table II. The results are given in Table II, and show the effects of hydrogen, iridium and ruthenium on the rhodium/iodide ion catalyst system for the methanol carbonylation process. As can be seen in Table II, the presence of hydrogen in the carbon monoxide feed has the effect of increasing the carbonylation rate in the rhodium/iodide ion catalyst system at the expense of increased impurity formation particularly acetaldehyde and unsaturated aldehydes such as crotonaldehyde and 2-ethyl crotonaldehyde(K vs. L). This presence of hydrogen in the carbon monoxide feed is often unavoidable, as commercial sources of carbon monoxide feedstock frequently contain hydrogen as an impurity. However, the addition of iridium to the rhodium/iodide ion catalyst system significantly decreases the formation of acetaldehyde, crotonaldehyde, and 2-ethyl crotonaldehyde when hydrogen is present in the carbon monoxide feed (L vs. M). The results of continuous operation, indicate that the addition of iridium to the catalyst system of rhodium/iodide ion, even in the presence of hydrogen in the carbon monoxide feed enhances the carbonylation rate from 20 to 23 mol/L-hr (K vs. M). Further rate improvement to 26 STY can be achieved by adding ruthenium into the rhodium/iridium/iodide ion catalyst system (N). As the amount of iridium in the system is increased, from 830 ppm to 2060 ppm, STY increases from 23 to 26 mole/L-hr, without an increase in the concentration of acetaldehyde and unsaturated aldehydes (M vs. O). Another benefit of addition of iridium into the rhodium/iodide ion catalyst system is the significant improvement in formation of impurities, particularly, of the unsaturates. The base case with rhodium/iodide ion catalyst system generates a total of about 10 ppm unsaturates in the reactor. With the presence of iridium, the unsaturates are lowered significantly (L vs. M). When ruthenium is added to the rhodium/iridium/iodide catalyst system, STY increases from 23 to 26 mole/L-hr, acetaldehyde concentration in the reactor decreases slightly from 530 to 517 ppm (M vs. N), and propionic acid concentration increases slightly, from 230 to 271 ppm in the product.

TABLE II

Continuous Operation Results[1,2,3]

|  | Rh/LiI/Ir<br>I | Rh/LiI<br>K | Rh/LiI/$H_2$<br>L | Rh/Ir/LiI/$H_2$<br>M | Rh/Ir/LiI/Ru/$H_2$<br>N | Rh/Ir/LiI/$H_2$<br>O |
|---|---|---|---|---|---|---|
| Total time (hrs) | 11 | 9 | 12 | 11 | 9 | 14 |
| LiI (wt %) | 10 | 11 | 12 | 11 | 10 | 11 |
| Rh (ppm) | 570 | 650 | 634 | 650 | 680 | 703 |
| Ir (ppm) | 900 | 0 | 0 | 830 | 930 | 2060 |
| Ru (ppm) | 0 | 0 | 0 | 0 | 650 | 0 |
| $H_2$ in CO feed (ppm) | 0 | 0 | 1850 | 1786 | 1800 | 2060 |
| Water (wt %) | 3.1 | 3.0 | 2.0 | 3.0 | 2.3 | 2.8 |
| MeI (wt %) | 11.2 | 12.0 | 11.3 | 12.8 | 11.7 | 11.0 |
| MeOAc (wt %) | 3.0 | 3.1 | 3.1 | 2.8 | 3.0 | 2.8 |
| Acid STY (mol/L-hr) | 22 | 20 | 21 | 23 | 26 | 26 |
| Reactor |  |  |  |  |  |  |
| Acetaldehyde (ppm) | 410 | 423 | 700 | 530 | 517 | n.d. |
| Unsaturates (ppm) | 0 | 2 | 10 | 0 | 0 | n.d. |
| Condensed flasher overhead |  |  |  |  |  |  |
| Acetaldehyde (ppm) | n.d. | 1500 | 2600 | 3000 | 2000 | 2650 |
| Unsaturates (ppm) | n.d. | 8 | 35 | 0 | 0 | 0 |
| Product |  |  |  |  |  |  |
| Unsaturates (ppm) | 0 | 0 | 5 | 0 | 0 | 0 |
| Propionic acid (ppm) | 160 | 75 | 150 | 230 | 271 | 220 |

[1] n.d. = not determined
[2] Reaction temperature was 195° C. at 400 psig
[3] Unsaturates = crotonaldehyde + 2-ethylcrotonaldehyde

What is claimed is:

1. In a process for producing acetic acid by reacting methanol with a carbon monoxide feed in a liquid reaction medium containing a catalyst comprising a rhodium salt and an iridium salt, and comprising water, acetic acid, methyl iodide, and methyl acetate and subsequently recovering acetic acid from the resulting reaction product, the improvement which comprises: maintaining in said reaction medium during the course of said reaction about a finite amount to less than 14 wt % of water together with (a) an effective amount of iodide ion in the range of about 2 to 20 wt % as catalyst stabilizer/co-promoter selected from the group consisting of alkali metal and alkaline earth metal salts, quaternary ammonium, phosphonium iodide salts, (b) about 5 wt % to 30 wt % of methyl iodide, and (c) about 0.5 wt % to 30 wt % of methyl acetate.

2. The process of claim 1 wherein said metal salt is a lithium salt.

3. The process of claim 2 wherein said lithium salt is lithium iodide.

4. The process of claim 2 wherein said lithium salt is lithium acetate.

5. The process of claim 1 wherein the rhodium salt is maintained in said reaction medium in a concentration of about 100 ppm to about 5000 ppm and the iridium is maintained in said reaction medium in a concentration of about 100 ppm to about 5000 ppm.

6. The process of claim 1 wherein the catalyst further comprises a transition metal salt selected from the group consisting of salts of ruthenium, tungsten, osmium, nickel, cobalt, platinum, palladium, manganese, titanium, vanadium, copper, aluminum, tin and antimony.

7. The process of claim 1 wherein the catalyst further comprises a ruthenium salt.

8. The process of claim 1 wherein there is maintained in the reaction medium about a finite amount to less than 14 wt % water, about 2 to 20 wt % iodide ion as lithium iodide, about 5 to 30 wt % methyl iodide, and about 0.5 to 30 wt % methyl acetate, with the balance consisting essentially of acetic acid.

9. The process of claim 8 comprising maintaining in said reaction medium during the course of said reaction about 0.1 wt % to about 8 wt % water.

10. The process of claim 1 wherein said metal salt is lithium iodide and maintaining in said reaction medium during the course of said reaction, about 5 to 15 wt % methyl iodide, about 1 to 20 wt % methyl acetate with the balance consisting essentially of acetic acid.

11. The process of claim 1 wherein the iodide ion in the reaction medium is about 10 to 20 wt %.

12. The process of claim 1 further comprising hydrogen in the carbon monoxide feed at a level greater than about 5 ppm.

* * * * *